US00PP14284P29

(12) United States Plant Patent
Moonen

(10) Patent No.: US PP14,284 P2
(45) Date of Patent: Nov. 11, 2003

(54) VERBENA PLANT NAMED 'KIEVERSTEM'

(50) Latin Name: *Verbena hybrida*
Varietal Denomination: Kieverstem

(75) Inventor: Carla Moonen, Enkhuizen (NL)

(73) Assignee: Kieft Seeds Holland, Venhuizen (NL)

( * ) Notice: Subject to any disclaimer, the term of this patent is extended or adjusted under 35 U.S.C. 154(b) by 0 days.

(21) Appl. No.: 10/259,941

(22) Filed: Sep. 29, 2002

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2003/01, GTI Jouve Retrieval Software, Citation for 'Kieverstem'.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Verbena plant named 'Kieverstem', characterized by its compact, upright and mounded plant habit; freely branching habit; dark green-colored leaves; and light purple and purple bi-colored flowers.

1 Drawing Sheet

Botanical classification/cultivar designation: *Verbena hybrida* cultivar Kieverstem.

BACKGROUND OF THE INVENTION

The present Invention relates to a new and distinct cultivar of Verbena plant, botanically known as *Verbena hybrida,* and hereinafter referred to by the name 'Kieverstem'.

The new Verbena was discovered by the Inventor in 1999 as a naturally-occurring whole plant mutation of an unnamed *Verbena hybrida* seedling selection, not patented, in a greenhouse in Venhuizen, The Netherlands. The new Verbena was selected by the Inventor on the basis of its unique flower color and compact growth habit.

Asexual reproduction of the new cultivar by terminal cuttings taken in a controlled environment in Venhuizen, The Netherlands, since 1999, has shown that the unique features of this new Verbena are stable and reproduced true to type in successive generations of asexual reproduction.

SUMMARY OF THE INVENTION

The following traits have been repeatedly observed and are determined to be the unique characteristics of 'Kieverstem'. These characteristics in combination distinguish 'Kieverstem' as a new and distinct cultivar:

1. Compact, upright and mounded plant habit.
2. Freely branching habit.
3. Dark green-colored leaves.
4. Light purple and purple bi-colored flowers.

Plants of the new Verbena differ primarily from plants of the mutation parent in flower color as plants of the unnamed selection had solid purple-colored flowers.

Plants of the new Verbena can be compared to plants of the cultivar Kievergrang, not patented. In side-by-side comparisons conducted in Venhuizen, The Netherlands, plants of the new Verbena differed primarily from plants of the cultivar Kievergrang in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description which accurately describe the colors of the new Verbena.

The photograph at the top of the sheet comprises a side perspective view of a typical flowering plant of 'Kieverstem' grown in a container.

The photograph at the bottom of the sheet comprises a close-up view of typical inflorescences and leaves of 'Kieverstem'.

DETAILED BOTANICAL DESCRIPTION

The cultivar Kieverstem has not been observed under all possible environmental conditions. The phenotype may vary somewhat with variations in environment such as temperature and light intensity without, however, any variance in genotype. The aforementioned photographs and following observations and measurements describe plants grown in Lompoc, Calif, under commercial practice during the winter and spring in a polycarbonate-covered greenhouse with day temperatures about 18 to 24° C., night temperatures about 16 to 18° C., and light levels about 5,000 to 8,000 foot-candles. Cuttings were planted in 15.25-cm containers, pinched one time, and grown for about 13 weeks. In the following description, color references are made to The Royal Horticultural Society Colour Chart, 1995 Edition, except where general terms of ordinary dictionary significance are used.

Botanical classification: *Verbena hybrida* cultivar Kieverstem.

Parentage: Naturally-occurring whole plant mutation of unnamed *Verbena hybrida* seedling selection, not patented.

Propagation:

*Type cutting.*—Terminal cuttings.

*Time to initiate roots, winter and summer.*—About 12 days at 21° C.

*Time to produce a rooted cutting or liner.*—Summer: About 21 days at 21° C. Winter: About 28 days at 21° C.

*Root description.*—Fine; white in color.

*Rooting habit.*—Freely branching.

Plant description:

*Form.*—Compact, upright and mounded plant habit.

*Growth and branching habit.*—Vigorous and freely-branching with about 18 lateral branches developing after the pinch, dense and bushy growth.

*Plant height.*—About 21 cm.

*Plant diameter or spread.*—About 25.5 cm.

*Lateral branches.*—Length: About 17 cm. Diameter: About 2 mm. Internode length: About 3.25 cm. Texture: Pubescent. Color: 144B.

*Foliage description.*—Arrangement: Opposite, simple. Length: About 5.5 cm. Width: About 2 cm. Shape: Oblong to deltoid. Apex: Acute. Base: Acute to attenuate. Margin: Irregularly crenate. Texture, upper and lower surfaces: Coarse, pubescent. Venation pattern: Pinnate. Color: Young foliage, upper surface: 146A. Young foliage, lower surface: 147B. Fully expanded, upper surface: 147A. Fully expanded, lower surface: 147B. Venation, upper surface: 147B. Venation, lower surface: 145B. Petiole: Length: About 1 cm. Diameter: About 3.5 mm. Color: 146C.

Flower description:

*Flower type and habit.*—Single upright salverform bi-colored flowers arranged on terminal racemes; flowers sessile. Freely flowering with about 36 flowers and flower buds per raceme; about two to three racemes per lateral branch. Inflorescences positioned above and beyond the foliage. Flowers last about two to four days under greenhouse conditions. Flowers not persistent.

*Fragrance.*—Faint floral scent.

*Flowering season.*—In the garden, flowering is continuous from spring until fall.

*Inflorescence size.*—Diameter: About 6.5 cm. Height: About 3.2 cm.

*Flower size.*—Diameter: About 2.5 cm. Tube length: About 2.7 cm. Throat diameter: About 2 mm. Tube diameter, at base: About 2 mm.

*Flower buds.*—Rate of opening, from showing color to fully open flower: About 1 to 2 days. Length: About 1.5 cm. Diameter, apex: About 4 mm. Diameter, base: About 2 mm. Shape: Tubular. Color: 79B.

*Petals.*—Quantity/arrangement: Five per flower fused at base. Lobe length: About 1.3 cm. Lobe width: About 1.2 cm. Shape: Roughly cordate. Apex: Emarginate. Margin: Entire. Texture, upper and lower surfaces: Velvety, smooth. Color: When opening, upper surface: Ground color, 76B, covered with random flecks, 77A. When opening, lower surface: Ground color, 76B, covered with random flecks, 77B. Fully opened, upper surface: Ground color, 76D to close to 155D, covered with random flecks, 77B to 77D; towards throat, 155A. With subsequent development, ground color, 76D, covered with random flecks, 82B to 82C. Fully opened, lower surface: Ground color, 76D, covered with random flecks, 77C to 77D. Throat: Towards apex, 155D; towards base, 145D. Tube: 155C.

*Sepals.*—Quantity/arrangement: Five, fused into a tube. Length: About 1.5 cm. Diameter: About 2 mm. Shape: Ligulate. Apex: Acute. Margin: Entire. Texture, upper and lower surfaces: Coarse, pubescent. Color, upper surface: 143C. Color, lower surface: 143A.

*Peduncles.*—Length: About 4.5 cm. Diameter: About 1.5 mm. Angle: Upright to about 45° from vertical. Strength: Moderate. Color: 144A.

*Reproductive organs.*—Stamens: Quantity: Four. Anther shape: Ovoid. Anther length: Less than 1 mm. Anther color: 144C. Pollen amount: Scarce. Pollen color: 2D. Pistils: Quantity: One. Pistil length: About 2 cm. Stigma shape: Bi-parted. Stigma color: 144C. Style length: About 1.8 cm. Style color: 144D. Ovary color: 145A.

*Fruit/seed.*—Fruit and seed production has not been observed.

Disease/pest resistance: Plants of the new Verbena have not been observed to be resistant to pathogens and pests common to Verbena.

Temperature tolerance: Plants of the new Verbena have been observed to be tolerant to temperatures ranging from 2 to 40° C.

It is claimed:

1. A new and distinct cultivar of Verbena plant named 'Kieverstem', as illustrated and described.

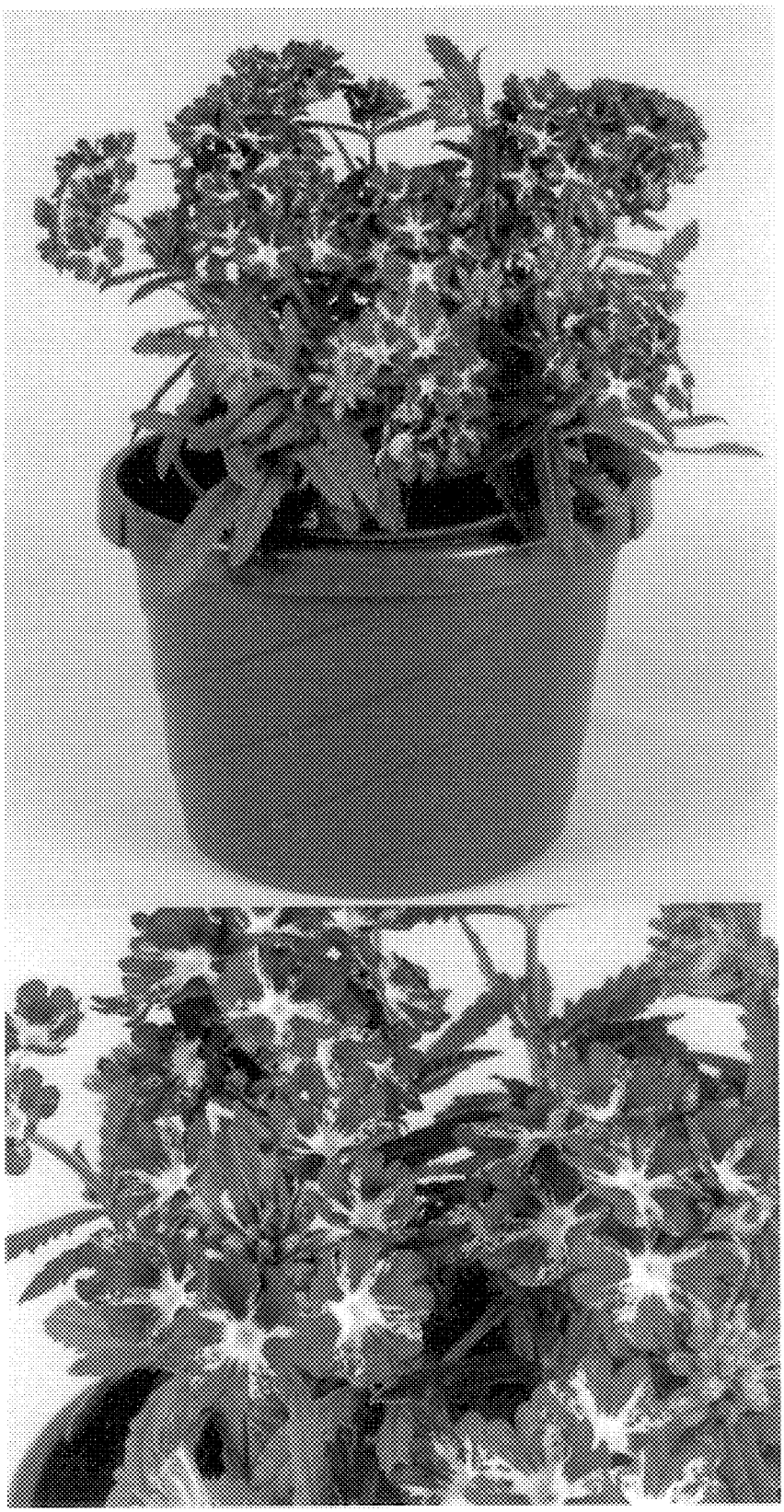

* * * * *